United States Patent
Nahm et al.

(10) Patent No.: US 8,621,661 B2
(45) Date of Patent: Dec. 31, 2013

(54) ELECTRICAL-MECHANICAL COMPLEX SENSOR FOR NANOMATERIALS

(75) Inventors: Seung Hoon Nahm, Daejeon (KR); Hoon Sik Jang, Daegu (KR); Sang Gu Jeon, Busan (KR); Min Seok Kim, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 13/821,708

(22) PCT Filed: Jan. 10, 2011

(86) PCT No.: PCT/KR2011/000145
§ 371 (c)(1),
(2), (4) Date: Mar. 8, 2013

(87) PCT Pub. No.: WO2012/096416
PCT Pub. Date: Jul. 19, 2012

(65) Prior Publication Data
US 2013/0167272 A1    Jun. 27, 2013

(51) Int. Cl.
*G01N 3/08* (2006.01)
*B81B 7/02* (2006.01)
*G01R 31/00* (2006.01)

(52) U.S. Cl.
USPC .................. 850/62; 850/44; 850/45

(58) Field of Classification Search
CPC ............... B81B 7/02; G01N 3/08; G01R 3/08
USPC ............................... 850/62, 44, 45
See application file for complete search history.

(56) References Cited

U.S. PATENT DOCUMENTS

| 7,360,422 | B2 * | 4/2008 | Madni et al. ............... 73/504.12 |
| 7,481,112 | B2 * | 1/2009 | Kim et al. .................. 73/514.33 |
| 7,958,782 | B2 * | 6/2011 | Phan Le ...................... 73/514.31 |
| 7,997,123 | B2 * | 8/2011 | Espinosa et al. ................ 73/105 |
| 8,161,805 | B2 * | 4/2012 | Su et al. .......................... 73/105 |
| 8,216,434 | B2 * | 7/2012 | Hsiai et al. ............... 204/192.15 |
| 8,264,941 | B2 * | 9/2012 | Tran et al. ..................... 369/126 |
| 8,461,936 | B2 * | 6/2013 | Vermeeren et al. ........... 331/154 |
| 2006/0179957 | A1 * | 8/2006 | Cook et al. ............... 73/862.041 |
| 2007/0063690 | A1 * | 3/2007 | De Wilde et al. ......... 324/117 R |
| 2008/0011058 | A1 | 1/2008 | Lal et al. |

FOREIGN PATENT DOCUMENTS

EP    2101181    9/2009
KR    10-0891613    4/2009

OTHER PUBLICATIONS

International Search Report mailed Oct. 13, 2011 for PCT/KR2011/000145.
Written Opinion From the ISA mailed Oct. 13, 2011 for PCT/KR2011/000145.
International Preliminary Report on Patentability issued Jul. 10, 2013, for PCT/KR2011/000145.
Written Opinion of the International Searching Authority mailed Oct. 13, 2011, for PCT/KR2011/000145.

* cited by examiner

*Primary Examiner* — David A Vanore
(74) *Attorney, Agent, or Firm* — Lowe Hauptman & Ham, LLP (57) ABSTRACT

Disclosed is an electrical-mechanical complex sensor for nanomaterials, including: a detector having a piezoelectric film therein, for measuring a mechanical property of a nanomaterial when a bending or tensile load is applied to the nanomaterial; a first detection film formed at an end of the detector to measure the mechanical property and an electrical property of the nanomaterial) in real time at the same time, when the nanomaterial contacts the first detection film; and a support to which one end of the detector is integrally connected, for supporting the detector.

4 Claims, 11 Drawing Sheets

ELECTRICAL-MECHANICAL COMPLEX SENSOR FOR NANOMATERIALS

TECHNICAL FIELD

The present invention relates to an electrical-mechanical complex sensor for nanomaterials, and more particularly, to an electro-mechanical complex sensor for nanomaterials which can measure electrical-mechanical properties at the same time.

BACKGROUND ART

The twenty first century may well be called an era of nanotechnology. For the last several decades, studies on nanotechnology have achieved excellent results, and more study results on and developments of nanotechnology are being expected.

Generally, nanomaterials refer to nanowires and nanorods having diameters ranging from less than 10 nm to several hundred nm.

Reliability evaluation methods and technologies for nanomaterials are necessarily required in an aspect of applications of nanotechnology, and accordingly a systematic mechanical property measuring and analyzing technology for nanomaterials needs to be developed.

Figure 7:
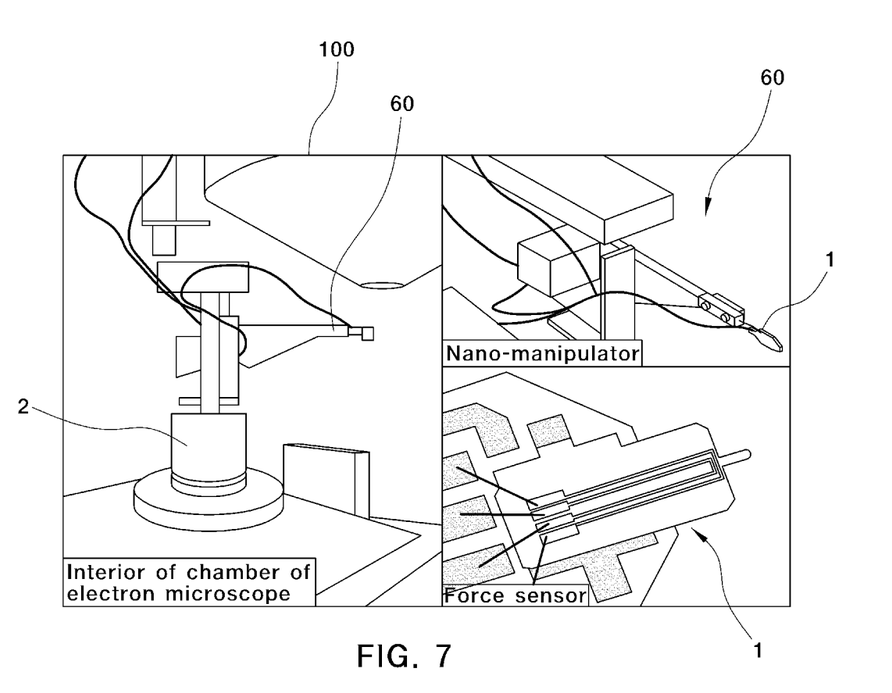
FIG. 7 is a picture representing a system for testing and measuring a mechanical property of a nanomaterial.

As shown in FIG. 7, a mechanical property measuring apparatus for nanomaterials includes an electron microscope 100 for observing and controlling a nano material 35, a nano-manipulator 60 mounted within the electron microscope 100 to control the nanomaterial 35 and perform a mechanical property test, and a force sensor 1 having a cantilever shape and controlled by the nano-manipulator 60. Load values can be obtained by using the force sensor 1 during a mechanical property test, and the results are numericalized by a computer.

The nano-manipulator 60 is installed within a scanning electron microscope 100 to be driven in a vacuum state, in which a feed through for data communication between an interior of a vacuum chamber and the outside is installed to maintain a vacuum state.

Further, the nano-manipulator 60 realizes 3-axis control at a minimum resolution of 10 nm for a smooth experiment for the nanomaterial 35, and since the nano-manipulator 60 needs to be precisely driven along the axes, a motor which can be minutely driven while not generating electromagnetic fields, that is, a piezoelectric nanomotor is mounted to the nano-manipulator to perform precise control such as minute manipulation in nano unit.

As shown in FIG. 7, the nano-manipulator 60 is configured to linearly moved along the X, Y, and Z axes, and the force sensor 1 and a tungsten tip may be replaced in a sensor holder 2 connected to the Z axis.

The nano-manipulator 60 is mounted at an upper portion of an interior of a chamber of the electron microscope 100 so that a body or an attachment of the nano-manipulator 60 cannot cover a detector in charge of an image of the electron microscope 100 to badly influence the image.

Further, the nano-manipulator 60 is controlled by a keyboard of a computer or a joystick through a control box called network control (NWC).

Then, a maximum movement distance of the nano-manipulator 60 along the axes is 20 mm.

The force sensor 1 serves to measure a load applied to the nanomaterial 35 when a bending or tensile load is applied to the nanomaterial 35 to measure a mechanical property of the nanomaterial 35.

As shown in FIG. 7, the force sensor 1 is of a cantilever type having a shape similar to that of an AFM tip, and it is easy to bond the nanomaterial 35 to the body of the sensor by using an electron beam of the electron microscope 100 during a tension test.

The body of the force sensor 1 is formed of $SiO_2$ and a piezoelectric material such as ZnO is applied on a $SiO_2$ surface, so that an infinitesimal force is applied from the outside, an electrical change due to compression or tension applied to a thin film while the cantilever is bent is converted into a mechanical value.

Then, an accurate load value can be obtained during a mechanical property test for the nanomaterial 35 by inputting a natural spring constant K of $SiO_2$ to perform a calibration.

Figure 8:
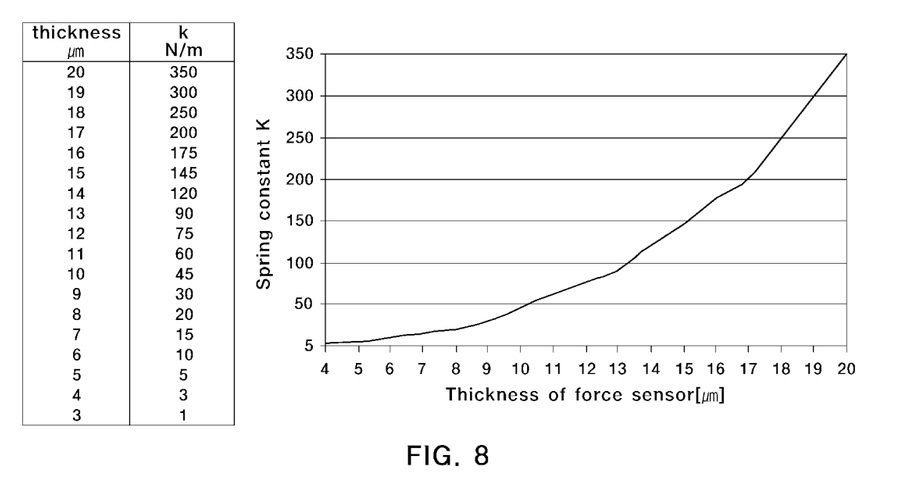
FIG. 8 is a graph depicting a relationship between a spring constant and a thickness of a force sensor according to the related art.

As shown in FIG. 8, a natural spring constant of $SiO_2$ varies according to a thickness of $SiO_2$, a resolution of the force sensor 1 depends on the K value, an average resolution of the force sensor 1 is 100 nN or less, and a maximum of several mN can be measured.

Figure 9:
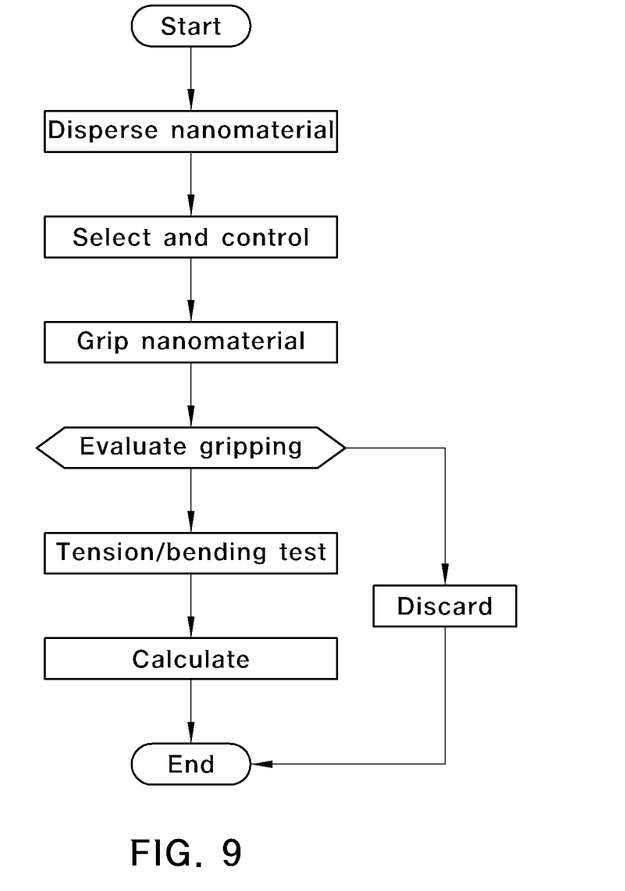
FIG. 9 is a flowchart of a mechanical property test for a nanomaterial.

FIG. 9 is a flowchart showing a method of testing a nano property according to a generally known mechanical property test procedure. First, the nanomaterial 35 in a powder state is dispersed, and then the nanomaterial 35 dispersed for a mechanical property test is selected by using the tungsten tip or the force sensor 1 and a location of the nanomaterial 35 is controlled.

If the nanomaterial 35 to be tested is determined, a tension or bending test is performed on the nanomaterial 35 after the nanomaterial 35 is gripped between the tungsten tip and the force sensor 1.

An electron beam of the electron microscope 100 is used to grip the nanomaterial 35 between the tungsten tip and the force sensor 1.

If the electron beam is scanned to a contact portion between the nano material 35 and the tungsten tip, carbon molecules and hydrocarbon molecules existing within the electron microscope 100 are deposited so that the nanomaterial 35 is gripped by the tungsten tip.

Then, if a gripping degree of the nanomaterial 35 is evaluated to be normal, tension and bending tests are performed, while if determined to be inferior, the nanomaterial 35 is wasted.

Figure 10:
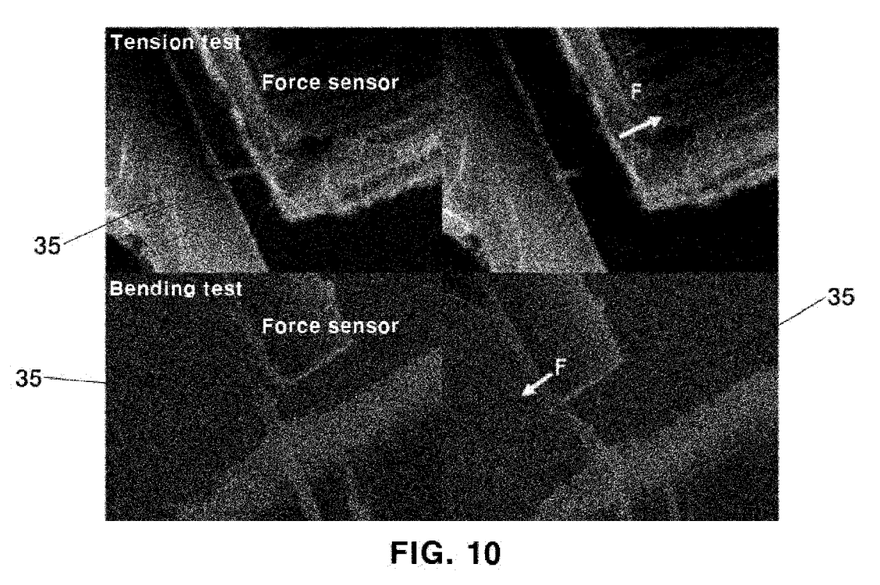
FIG. 10 is a picture representing examples of tension and bending tests for nanomaterials.

FIG. 10 is a picture showing an example of a tension/bending test for nanomaterials.

In order to perform a tension test for the nanomaterial 35, the nanomaterial 35 is made horizontal to an end of the force sensor 1 by vertically gripping the nanomaterial 35 by the tungsten tip or a rigid body and rotating the holder 2 of the electron microscope 100.

After the force sensor 1 and the nanomaterial 35 are horizontally positioned for an accurate measurement during the tension test, the force sensor 1 and an end of the nanomaterial 35 are gripped by using an electron beam of the electron microscope 100 and a tension test is performed on the nanomaterial 35.

According to the tension test method, the nano-manipulator 60 is adjusted by using a joystick, a tensile force is applied to the nanomaterial 35 gripped by an end of the force sensor 1 if the force sensor 1 is pulled by using the nano-manipulator 60, and the force sensor 1 converts an electrical change due to a tension applied to a piezoelectric material into a mechanical value.

Further, a mechanical property is evaluated by using a spring constant K of the force sensor 1.

The force sensor 1 is positioned on the right side of the nanomaterial 35 to perform a bending test on the nanomaterial 35, and the force sensor 1 and the nanomaterial are positioned perpendicular to each other for an accurate measurement.

Then, the nanomaterial 35 and the force sensor 1 are not gripped but a bending test is performed after a position of the force sensor 1 is determined.

According to the bending test method, the nano-manipulator 60 is adjusted by using a joystick, and the nanomaterial is deflected by moving the force sensor 1 by using the nano-manipulator 60.

The bending test is performed not until the nanomaterial 35 is fractured and within a range where a nonlinear section is not generated as the force sensor 1 and the nanomaterial 35 are slid with respect to each other.

Figure 11:
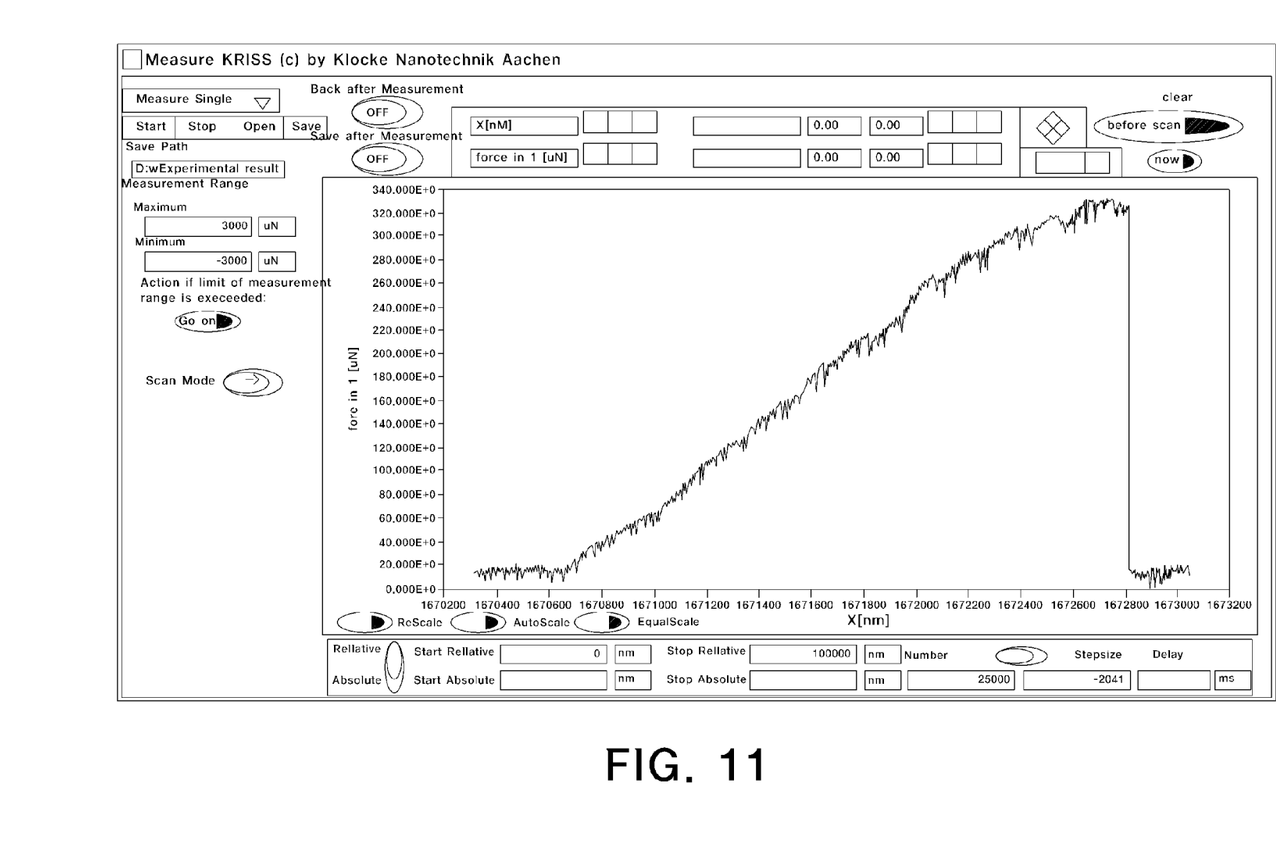
FIG. 11 is a picture representing sample data of a mechanical property test for a nanomaterial.

If tests of mechanical properties, that is, tension and bending tests are performed on the nanomaterial 35 by using the nano-manipulator 60 and the force sensor 1 in this way, a displacement-load graph of FIG. 11 is obtained, a strain-stress graph can be obtained from FIG. 11, a modulus of elasticity of the nanomaterial 35 can be obtained from the strain-stress graph, and a tensile strength and a percentage of elongation of the nanomaterial 35 can be obtained Thus, reliability of nanomaterials 35 can be evaluated and reliability of nano and micromaterials can be predicted by comprehending characteristics of nanomaterials 35 through mechanical property test using the nano-manipulator 40 and the force sensor 1 and creating a database for mechanical property test results on the nanomaterials 35, allowing mechanical property test services for various nanomaterials 35.

However, since only measurement of mechanical properties of nanomaterials 35 is given undue stress to the force sensor 1 according to the related art, a sensor capable of measuring a mechanical property and an electrical property at the same time is required.

DETAILED DESCRIPTION OF THE INVENTION

Technical Problem

Therefore, the present invention has been made in view of the above-mentioned problems, and an aspect of the present invention is to provide an electrical-mechanical complex sensor which can measure mechanical and electrical properties in real time at the same time when a load is applied to a nanomaterial such as a carbon nanotube to measure and evaluate a correlation between mechanical characteristics and electrical characteristics, thereby improving an evaluation of reliability of a nanomaterial.

Technical Solution

In accordance with an aspect of the present invention, there is provided an electrical-mechanical complex sensor for nanomaterials for measuring mechanical and electrical properties at the same time as compared with an existing force sensor for measuring only a mechanical property of a nanomaterial, wherein a detector has a lamination structure of $SiO_2$/an Au layer/a piezoelectric film (ZnO)/an Au layer/$SiO_2$ so that a load applied to the nanomaterial is measured by using a piezoelectric phenomenon of a piezoelectric film generated when a tensile load is applied by bringing a first detection film formed at an end of a detector to apply a bending load or grip the nanomaterial.

Advantageous Effects

The advantage of the electrical-mechanical complex sensor for nanomaterials according to the present invention is as follows.

A first detection film formed at an end of a detector and a second detection film formed at an end of an electrode for measuring electrical characteristics are connected to each other through a carbon nanotube yarns and an end of the detector contacts a nanomaterial or is gripped, so that electrical and mechanical properties of a nanomaterial can be measured at the same time while a bending load or a tensile load is applied to the nanomaterial, thereby making it possible to measure and evaluate a correlation between mechanical characteristics and electrical characteristics and improving an evaluation of reliability of the nanomaterial.

DESCRIPTION OF REFERENCE NUMERALS FOR MAIN PARTS

10: Support 11: First electrode
12: Second electrode 13: Third electrode
14: Fourth electrode 15: Fifth electrode
20: Detector 21: Detection film
22: Silicon oxide film ($SiO_2$)
23: Au layer
24: Piezoelectric film (ZnO)
25: Pt
30: Carbon nanotube yarns
35: Nano material
40: Complex sensor
50: Tungsten tip
51: Stage
60: Nano-manipulator
70: Multi-meter
80: Voltage source
90: Computer
100: Electron Microscope

MODE FOR CARRYING OUT THE INVENTION

Hereinafter, an exemplary embodiment of the present invention will be described in detail with reference to the accompanying drawings.

Figure 1:
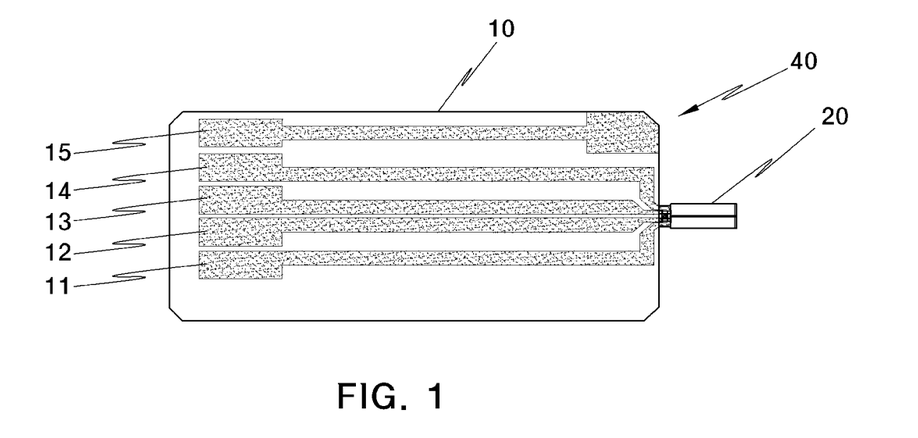
FIG. 1 is a plan view showing an electrical-mechanical complex sensor according to an embodiment of the present invention.
Figure 2:
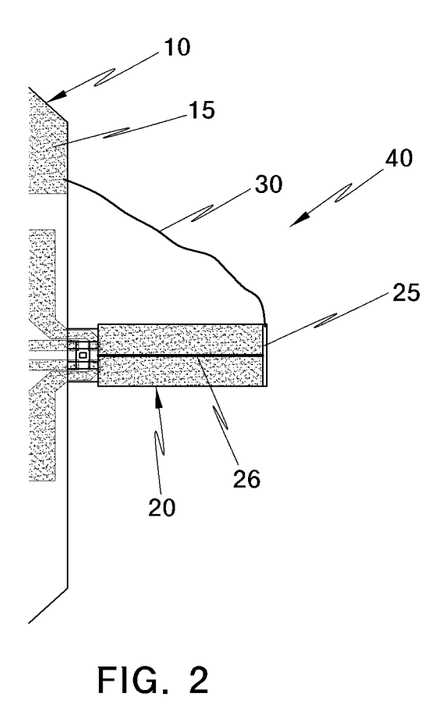
FIG. 2 is a partial view of FIG. 1.
Figure 3:
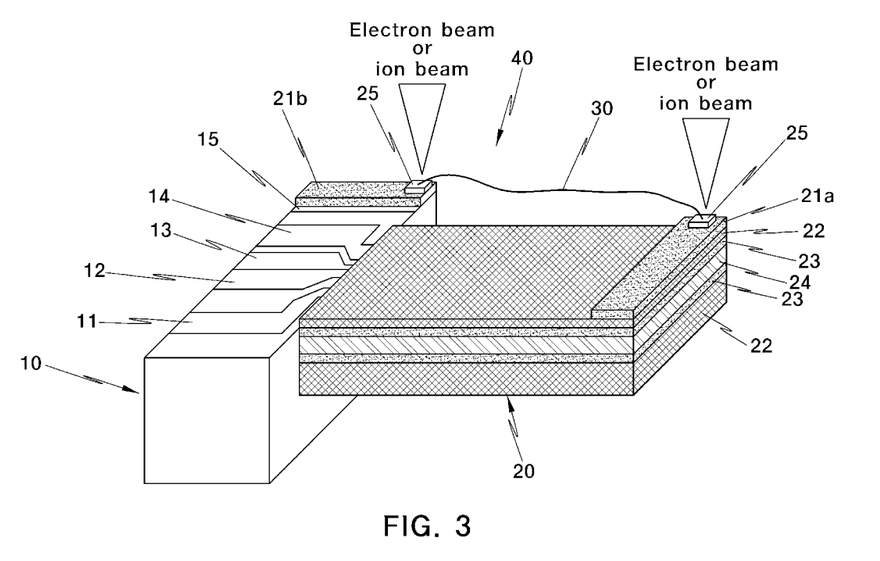
FIG. 3 is a partial perspective view of FIG. 1.
Figure 4:
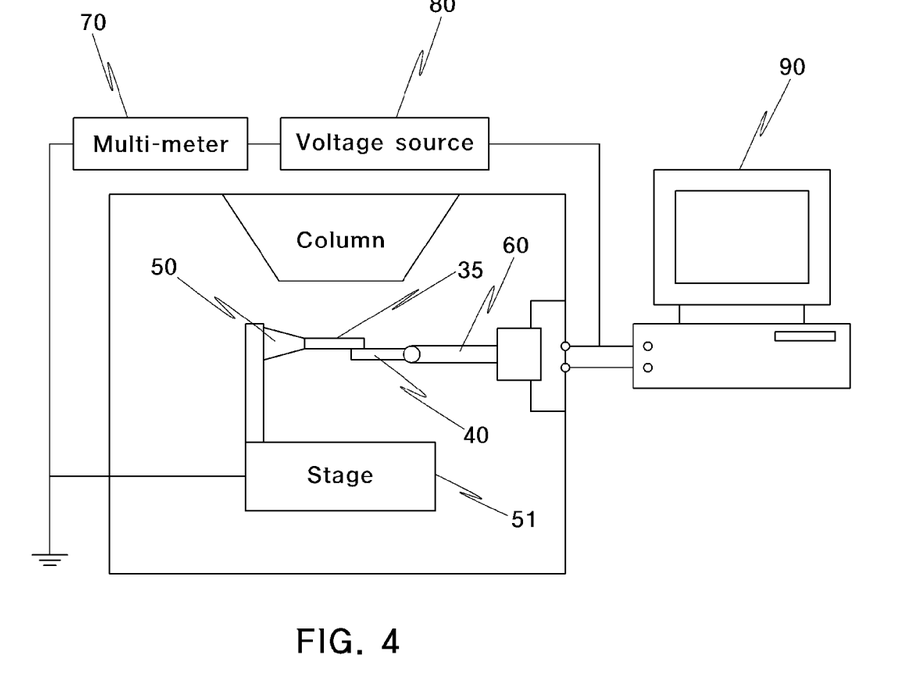
FIG. 4 is a schematic view showing an electrical-mechanical complex sensor for nanomaterials according to the embodiment of the present invention.

FIG. 1 is a plan view showing an electrical-mechanical complex sensor according to an embodiment of the present invention. FIG. 2 is a partial view of FIG. 1. FIG. 3 is a partial perspective view of FIG. 1. FIG. 4 is a schematic view showing an electrical-mechanical complex sensor for nanomaterials according to the embodiment of the present invention.

The present invention can measure electrical-mechanical complex properties of a nanomaterial 35 in real time at the same time to measure and evaluate correlations between mechanical characteristics and electrical characteristics and improve evaluation of a reliability of the nanomaterial 35.

The electrical-mechanical complex sensor 40 for nanomaterials according to the embodiment of the present invention includes a support 10 and a detector 20.

The support 10 supports the detector 20 in the form of a cantilever and at least five electrodes are formed on an upper surface of the support 10. Among the electrodes, the first to fourth electrodes 11 to 14 from the bottom are used as a Wheatstone bridge circuit for measuring a tension and a bending load corresponding to mechanical properties from the detector 20, ends of the four electrodes, that is, the first to fourth electrodes 11 to 14 are electrically connected to the detector 20, and electrode terminals are formed at opposite ends of the four electrodes 11 to 14.

Then, the electrode terminals are connected to an external voltage source 80 to receive electric power.

The detector 20 is formed in the form of a cantilever one end of which is supported by the support 10, and a silicon oxide film ($SiO_2$) 22, an Au layer 23, a piezoelectric film (ZnO) 24, an Au layer 23, and a silicon oxide film ($SiO_2$) 22 are laminated in the detector 20 from the bottom.

Then, if an infinitesimal force is applied from the outside, a tensile or compressing force is applied to the piezoelectric film 24 while the detector 20 in the form of a cantilever is defected so that an electrical change can be converted to a mechanical value.

Then, the mechanical value is calibrated by inputting K which is a spring constant of the silicon oxide film ($SiO_2$) to obtain an accurate load value during a mechanical property test of the nanomaterial 35.

Here, the fifth electrode 15 which is the remaining one of the electrodes is used as an electrode for measuring electrical characteristics.

A first detection film 21a of Au is formed at an end of the detector 20, a second detection film 21b of Au is formed in the fifth electrode 15 of the support 10, and opposite ends of a carbon nanotube yarns 30 are attached to the first detection film 21a and the second detection film 21b such that a current flows through the carbon nanotube yarns 30, making it possible to measure an electrical property of the nanomaterial 35.

Then, in order to increase electrical conductivities between the carbon nanotube yarns 30 and the first and second detection films 21a and 21b, Pt 25 is deposited by using a focused ion beam (FIB) or carbon molecules or hydrocarbon molecules are deposited by using an electron beam on the first and second detectors 21a and 21b to which opposite ends of the carbon nanotube yarns 30 are attached.

If the electron beam is scanned to contact portions between the carbon nanotube yarns 30 and the first detection film 21a, and between the carbon nanotube yarns 30 and the second detection film 21b, the carbon molecules or hydrocarbon molecules in the interior of the electron microscope 100 are deposited and the carbon nanotube yarns 30 is gripped by the first and second detection films 21a and 21b.

An omni probe or a tungsten tip 50 is used to attach or control the carbon nanotube yarns 30, and the omni probe or the tungsten tip 50 may be controlled by using the FIB or the nano-manipulator 60 attached within the electron microscope 100.

The complex property measuring apparatus using the electrical-mechanical complex sensor 40 according to the embodiment of the present invention includes a complex sensor 40, a tungsten tip 50, a nano-manipulator 60, a computer 90, a multi-meter 70, and a voltage source 80.

The complex sensor 40 serves to measure mechanical and electrical characteristics of the nanomaterial 35 at the same time.

The tungsten tip 50 serves to attach or control the carbon nanotube yarns 30 between the first detection film 21a formed at an end of the detector 20 of the complex sensor 40 and the second detection film 21b of the fifth electrode 15, or grip the nanomaterial 35 to control the nanomaterial 35 during the tension or bending tests.

Then, the tungsten tip 50 is configured to be moved upward, downward, leftward, and rightward in the stage 51.

The nano-manipulator 60 is mounted within a scanning electron microscope 100 to serve to control the complex sensor 40 and is driven in a vacuum state, and a feed through for data communications between an interior and an exterior of the vacuum chamber is installed to maintain a vacuum state.

The nano-manipulator 60 is configured to be linearly moved along the X, Y, and Z axes at a resolution of a minimum of 10 nm for a smooth test of the nanomaterial 35.

The nano-manipulator 60 is required to be precisely driven along the axes, in which case electromagnetic fields generated in the drive motor should not badly influence an image of the electron microscope 100.

Thus, according to the present invention, a piezoelectric nanomotor as a motor which can be minutely driven while not generating electromagnetic fields may be mounted for a precise control such as a minute manipulation in nano unit.

The nano-manipulator 60 is mounted at an upper portion of an interior of the chamber of the electron microscope 100, and the body or attachments of the nano-manipulator 60 is mounted not to cover a detector in charge of an image of the electron microscope 100, not badly influencing the image.

Further, the nano-manipulator 60 is configured to be precisely controlled by a keyboard of a computer or a joystick through a control box called a network control.

The voltage source 80 is electrically connected to the nano-manipulator 60 and the stage 51 to apply electric power necessary for measuring electrical-mechanical characteristics to an electrode of the complex sensor 40.

The multi-meter 70 measured a voltage, a current, and a resistance of the voltage source 80.

Hereinafter, a method of measuring a tension and a bending load by using the electrical-mechanical complex sensor 40 according to the embodiment of the present invention, and measuring varying electrical characteristics (voltage, current, and resistance) at the same time will be described.

For an electrical-mechanical property test of the nanomaterial 35, a suitable nanomaterial 35 is first selected.

That is, the nanomaterial 35 in the form of powder is dispersed, the nanomaterial 35 dispersed for a mechanical property test is selected by using the tungsten tip 50 or the complex sensor 40, and a position of the nanomaterial 35 is controlled.

If the nanomaterial 35 to be tested is determined, the nanomaterial 35 is gripped.

After the nanomaterial 35 is gripped between the tungsten tip 50 and the complex sensor 40, tension and bending tests are performed.

The tests are performed at room temperature, and 6 or more hours of stabilization time is required for stabilization after the complex sensor 40 and the material are installed. Further, since the manipulation in nano unit is influenced even by minute vibrations, vibrations are removed by using an anti-vibration pad, and an action or equipment which may cause vibrations is prohibited.

An electron beam of the electron microscope 100 is used to grip the nanomaterial 35. If the electron beam is scanned to a contact portion between the nanomaterial 35 and the tungsten tip 50, the carbon molecules or hydrocarbon molecules in the electron microscope 100 are deposited to allow the nanomaterial 35 to be gripped by the tungsten tip 50.

Then, in order to evaluate a gripping degree of the nanomaterial 35, after the tungsten tip 50 is electrically connected to the nano multi-meter 70 through the feed screw within the electron microscope 100 and is brought into contact with the nanomaterial 35 and the tungsten tip 50, a resistance of a current flowing through the nanomaterial 35 and the tungsten tip 50 is measured by the multi-meter 70 in the gripping step by irradiating an electron beam to the contact portion in a vacuum atmosphere.

It is determined while performing the gripping whether an initially measured resistance is lowered by a set rate within a predetermined lapse of time in measuring an electrical resistance.

If the resistance is lowered by the set rate, it may be determined that the gripping is normal and tension and bending tests may be performed, and otherwise, it is determined that the nanomaterial is inferior and the nanomaterial is wasted.

Next, a tension test is performed.

In order to perform the tension test, an end of the complex sensor 40 is made horizontal to the nanomaterial 35 by adjusting the nano-manipulator 60.

The nano-manipulator 60 is adjusted by a joystick of the computer, and since the nano-manipulator 60 can be moved only along three axes during the measurement, the nano-manipulator 60 is positioned on the right side of the nanomaterial 35 and the complex sensor 40 and the nanomaterial 35 are disposed horizontally.

Thereafter, a tension test for nanomaterials 35 is performed while the first detection film 21a of the complex sensor 40 and an end of the nanomaterial 35 are gripped by using an electron beam of the electron microscope 100.

The tension test is performed in a displacement control method by using a network control, a tensile load applied to the nanomaterial 35 is measured through the detector 20 of the complex sensor 40 every 2 nm while tension speed is 10 nm/s.

Further, electrical characteristics (voltage, current, and resistance) changed at the same time when the tensile load is applied to the nanomaterial 35 are measured by the second detection film 21b connected to the first detection film 21a of the detector 20 through the carbon nanotube yarns 30.

In more detail, a current is allowed to flow to the electrodes by turning on the computer 90 and applying a voltage to the nano-manipulator 60 and an electrode of the complex sensor 40.

Here, when a voltage is applied to the first to fourth electrodes 11 to 14 constituting the Wheatstone bridge circuit and a voltage is applied to the detector 20 electrically connected to the first to fourth electrodes 11 to 14 and the first detection film 21a at an end of the detector 20, a current of the first detection film 21a flows to the second detection film 21b formed at an end of the fifth electrode 15 of the support 10 through the carbon nanotube yarns 30.

Then, if a voltage is applied to the piezoelectric film 24 of the detector 20, the piezoelectric film 24 is prolonged in a direction in which a voltage is applied, and according to the characteristics of the piezoelectric material contracted in a direction perpendicular to a direction in which the voltage is applied, if a tensile load is applied to the nanomaterial 35, an electrical change is converted to a mechanical change by using the piezoelectric phenomenon, making it possible to calculate the applied tensile load.

Further, since the electrical characteristics of the nanomaterial 35 vary as a bending load and a tensile load are applied to the nanomaterial 35, a difference between electrical signals flowing through the fifth electrode 15 due to electrical characteristics of the nanomaterial 35 before the tensile load is applied and electrical characteristics of the nanomaterial 35 after the tensile load is applied is measured so that the electrical characteristics of the nanomaterial 35 can be recognized while a current applied to the first detection film 21a of the detector 20 flows to the second detection film 21b of the fifth electrode 15 through the carbon nanotube yarns 30.

For a bending test for nanomaterials 35, a cantilever bending test is performed.

The complex sensor 40 is positioned on the right side of the nanomaterial 35, and the complex sensor 40 and the nanomaterial 35 are positioned perpendicular to each other for an accurate measurement.

The nanomaterial 35 and the complex sensor 40 are not gripped, and the bending test is performed after a position of the complex sensor 40 is determined.

The bending test is performed not until the nanomaterial 35 is fractured and within a range where a nonlinear section is not generated as the complex sensor 40 and the nanomaterial 35 are slid with respect to each other. During the bending test, a method of measuring a bending load and electrical characteristics is the same as the tension test.

Figure 5:
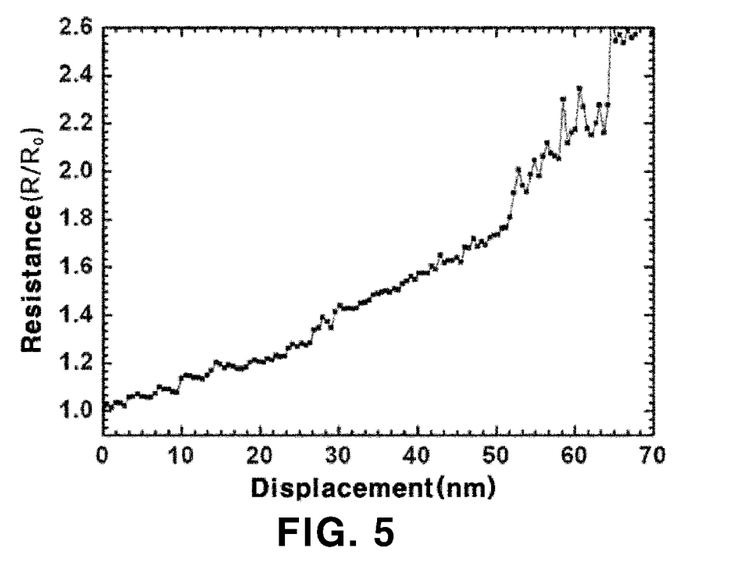
FIG. 5 is a graph depicting a change in resistance according to a displacement of a nanomaterial.
Figure 6:
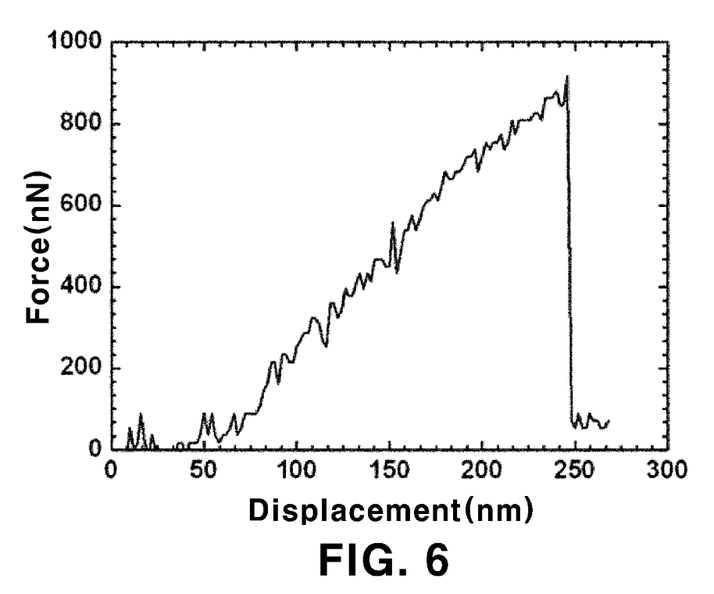
FIG. 6 is a graph depicting a change in force (load) according to a displacement of a nanomaterial.

Here, FIG. 5 is a graph depicting a change in resistance according to a displacement of a nanomaterial 35. FIG. 6 is a graph depicting a change in force (load) according to a displacement of a nanomaterial 35.

By performing a tension or bending test on the nanomaterial 35, the displacement-load (mechanical property) or displacement-resistance (electrical property) graph as in FIGS. 5 and 6 can be obtained, correlations between mechanical characteristics and electrical characteristics can be measured and evaluated, and evaluation of a reliability of the nanomaterial 35 can be improved.

The invention claimed is:

1. An electrical-mechanical complex sensor for nanomaterials, comprising:
a detector (20) having a piezoelectric film therein, for measuring a mechanical property of a nanomaterial (35) when a bending or tensile load is applied to the nanomaterial (35);
a first detection film (21a) formed at an end of the detector (20) to measure the mechanical property and an electrical property of the nanomaterial (35) in real time at the same time, when the nanomaterial (35) contacts the first detection film (21a); and
a support (10) to which one end of the detector (20) is integrally connected, for supporting the detector (20),
wherein the support (10) comprises first to fourth electrodes (11 to 14) constituting a Wheatstone bridge circuit to measure the load applied to the nanomaterial (35), and a fifth electrode (15) having a second detection film (21b) at an end thereof to be connected to a first detection film (21a), for measuring an electrical property of the nanomaterial (35).

2. The electrical-mechanical complex sensor of claim 1, wherein the detector (20) has a structure in which a silicon oxide film (22), an Au layer (23), a piezoelectric film (24) formed of a piezoelectric material, an Au layer (23), and a silicon oxide film (22) are laminated, and measures the applied load by using a piezoelectric phenomenon of the piezoelectric film (24).

3. The electrical-mechanical complex sensor of claim 1, wherein the first detection film (21*a*) and the second detection film (21*b*) are electrically connected to each other by a carbon nanotube yarns (30), and electron beams are scanned to contact portions between the first and second detection films (21*a*, 21*b*) and the carbon nanotube yarns (30) to deposit carbon molecules or hydrocarbon molecules.

4. The electrical-mechanical complex sensor of claim 1, wherein the first detection film (21*a*) and the second detection film (21*b*) are electrically connected to each other by a carbon nanotube yarns (30), and ion beams are scanned to contact portions between the first and second detection films (21*a*, 21*b*)and the carbon nanotube yarns (30) to deposit platinum.

* * * * *